United States Patent
Dunnavant et al.

[11] B 3,993,684
[45] Nov. 23, 1976

[54] MONOMERIC COMPOUNDS

[75] Inventors: William R. Dunnavant, Columbus, Ohio; Edward M. Harris, Webster Groves, Mo.; Philip F. Kurz; Richard A. Markle, both of Columbus, Ohio; Edward H. Parker, Ballwin, Mo.

[73] Assignee: Western Litho Plate & Supply Co., St. Louis, Mo.

[22] Filed: Aug. 3, 1973

[21] Appl. No.: 385,483

[44] Published under the second Trial Voluntary Protest Program on February 17, 1976 as document No. B 385,483.

Related U.S. Application Data

[62] Division of Ser. No. 173,661, Aug. 20, 1971, Pat. No. 3,799,915.

[52] U.S. Cl. .......................... 260/471 R; 526/298; 260/326.13 R; 260/332.2 A; 260/347.4; 260/465 D; 260/472; 260/469; 260/473 R; 260/476 R; 526/309; 526/312; 526/321

[51] Int. Cl.² ........................................ C07C 101/46

[58] Field of Search ........ 260/471 R, 476 R, 486 R, 260/486 AC, 469, 473 R, 472, 465 D

[56] References Cited
OTHER PUBLICATIONS
Finar, I. L. *Organic Chemistry*, vol. I (1931), pub. by Richard Clay & Co., Great Britain pp. 200 – 202 relied on.

*Primary Examiner*—Lorraine A. Weinberger
*Assistant Examiner*—L. A. Thaxton
*Attorney, Agent, or Firm*—Koenig, Senniger, Powers and Leavitt

[57] ABSTRACT
Photosensitive homopolymers and substantially non-crosslinked copolymers containing the recurring unit:

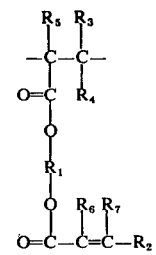

$R_1$ may be substituted or unsubstituted alkylene, aralkylene, alkoxyalkylene or aryloxyalkylene. $R_2$ is a substituted or unsubstituted aryl group or heterocyclic group having aromatic character. $R_3$, $R_4$, and $R_5$ are hydrogen, halogen or lower alkyl. $R_6$ and $R_7$ may be hydrogen, halogen, nitro, lower alkyl, phenyl, substituted phenyl, phenoxy and lower alkoxy. Lithographic plates bearing these photosensitive polymers can be stored without deterioration for extended periods prior to exposure, and produce highly abrasion resistant plates on being exposed. The photosensitive polymers of the invention are preferably produced by homopolymerization of novel monomers having the general formula

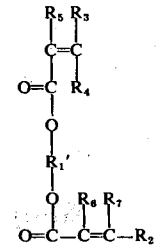

where $R_1{'}$ is alkylene, haloalkylene, alkoxyalkylene, aminoalkylene, cycloalkylene, aralkylene, cycloalkylalkylene, cyanoalkylene, and aryloxyalkylene, and $R_2$, $R_3$, $R_4$, $R_5$, $R_6$, and $R_7$ are as defined above; and by copolymerization of these monomers with one or more ethylenically unsaturated comonomers. Methods of preparing the photopolymers and the novel monomers are also disclosed, as are methods of preparing and exposing plates bearing the polymers.

11 Claims, No Drawings

MONOMERIC COMPOUNDS

This is a division of application Ser. No. 173,661, filed Aug. 20, 1971 now U.S. Pat. No. 3,799,915.

BACKGROUND OF THE INVENTION

This invention relates to the field of lithography and more particularly to novel photopolymers useful as light-sensitive coatings for lithographic plates, to novel monomers, homopolymers, and copolymers and to novel methods for preparing and using said monomers and polymers.

In the art of lithography, the instrument used for printing is an exposed and developed plate constituted by a hydrophilic oleophobic substrate covered in the image areas by an oleophilic hydrophobic coating. Typically, the substrate is a thin sheet of metal, such as aluminum, magnesium or zinc, and the coating corresponding to the image area to be produced consists of a water-insoluble material, for example, a diazo or azide compound. In printing the desired image on a surface, the plate is first contacted with a water solution which is repelled by the image areas, but retained by the non-printing areas. Then the plate is contacted with an oil-base ink which spreads uniformly over the image area but is repelled by the non-image areas of the substrate which have retained the water solution. The ink-laden plate is then pressed against the printing surface to produce the desired image on that surface.

To prepare a printing plate of the character described, a coating of a soluble light-sensitive material is applied uniformly over the surface of the substrate. Light is then projected through a transparent photograph (normally a negative) of the image onto the plate. In those areas where light passes through a negative and strikes the light-sensitive material, the latter is chemically converted into a hard water-insoluble oleophilic material. The areas of the coating unaffected by light retain the same chemical character that they originally possessed. A developer or solvent, such as water, an alkaline solution, gum arabic, or an organic solvent is then applied to the surface of the plate to dissolve and remove those portions of the coating which have not been subjected to light, leaving unaffected the image areas of the coating which have been converted by light into an insoluble material. The oleophilic layer remaining on the plate after treatment with the solvent thus assumes the configuration of the image to be printed. Positive working light-sensitive materials are also available. Such materials are initially insoluble in the developing solution but are converted to a soluble material where they are struck by light, and a developer is employed to dissolve the soluble material from the light-exposed areas. Exposure of plates coated with such materials is therefore effected by projection of light through a positive rather than a negative.

There are numerous light-sensitive resins or materials that can be used in preparing lithographic plates, and numerous processes by which such plates are produced. One process which provides a high quality plate is the so-called "Deep Etch" process wherein the plate is chemically etched in the exposed areas. However, the Deep Etch process is complex and expensive and the use of non-etched negative working plates largely predominates in this country. The light-sensitive materials which have found most common use in this country, until recently at least, are the so-called diazo resins, such as the condensation product of paraformaldehyde with the sulfate salt of paradiazodiphenyl amine (prepared as described in U.S. Pat. No. 2,714,066). Diazo type light-sensitive coatings for lithographic plates have proved satisfactory in many respects, but are rather fragile nd must be reinforced by developing lacquers in order to withstand the wear and tear of printing. Diazo coatings also suffer from the disadvantage of being subject to fairly rapid deterioration on storage after application to the surface of a plate, particularly on storage of the plate at elevated temperatures. Such deterioration results in part from reaction of the diazo material with the underlying metal substrate. Aluminum substrates, which in most other respects represent the preferred substrate material, present a particular problem with respect to deterioration of diazo type lightsensitive materials.

To avoid the problems associated with the use of diazo resins, efforts have been devoted in the art to the provision of base plates having barrier coatings designed to prevent reaction between the resin and the metal substrate, while other efforts have been devoted to the development of various photopolymers which are relatively unreactive with the substrate. Typical of the barrier layers which have been developed are those disclosed in U.S. Pat. Nos. 2,714,066, 3,020,210, 3,064,562, 3,136,636, 3,136,639, and 3,148,984. A substantial amount of research in the art has been allocated to the development of photopolymers. Illustrative patents which describe certain previously known photopolymers include 2,610,120, 2,691,584, 2,725,372, 2,751,296, and 2,835,656. The basic objective of most photopolymer research activity has been the provision of linear polymers soluble in a variety of solvents and having pendant groups which crosslink on exposure to light to produce a hard insoluble polymeric matrix.

Prominent among the efforts in this direction has been the development of the various polymers derived from vinyl cinnamate. Ideally, vinyl cinnamate can be polymerized through the vinyl group to produce a linear photopolymer having pendant cinnamate groups. On exposure to light, the cinnamate groups should be photo-crosslinkable to produce a hard insoluble substance which would serve as a printing surface for lithographic plates. Unfortunately, however, vinyl cinnamate suffers from certain serious drawbacks. Because of the relative proximity of the double bond of the vinyl group to the double bond of the cinnamate group, vinyl cinnamate suffers from an inordinate tendency to lactonize during attempts to polymerize it. Lactonization produces a product which is not light sensitive. Even if lactonization is avoided, however, polyvinyl cinnamate polymers have not proved to be fully satisfactory in use. Exposed polyvinyl cinnamate plates are relatively fragile and cannot be rub developed. They must be spray developed, which often results in incomplete removal of the unexposed polymer and consequent scumming during a printing run.

While certain other photopolymers developed heretofore have been reasonably satisfactory, they have not generally been capable of yielding a lithographic printing surface whose abrasion resistance is as great as might be desired. Certain of the other previously known photopolymers have also presented processing problems in their preparation and application to the surface of a lithographic plate. An unfulfilled need has existed in the art, therefore, for novel photopolymers

3 which avoid these problems, particularly as regards susceptibility to abrasion.

SUMMARY OF THE INVENTION

Among the several objects of the invention, therefore, may be noted the provision of soluble photopolymers which are photo-crosslinkable into abrasion resistant lithographic printing surfaces; the provision of such photopolymers which produce a printing surface that is resistant to wear under press conditions; the provision of soluble photopolymers which do not react with aluminum substrates; the provision of monomers from which such photopolymers may be produced; the provision of methods for preparing such monomers and polymers; the provision of methods for applying such polymers to lithographic plates; and the provision of methods for exposing and developing plates carrying such polymers. Other objects and features will be in part apparent and in part pointed out hereinafter.

Briefly, therefore, the present invention is directed to monomers represented by the general formula:

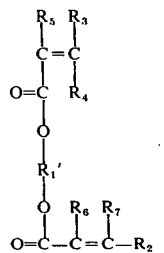

wherein $R_1'$ is selected from the group consisting of alkylene, haloalkylene, alkoxyalkylene, aminoalkylene, cycloalkylene, aralkylene, cycloalkylalkylene, cyanoalkylene, and aryloxyalkylene groups, $R_2$ is selected from the group consisting of substituted or unsubstituted aryl groups or heterocyclic groups having aromatic character, $R_3$, $R_4$ and $R_5$ are each selected from the group consisting of hydrogen, halogen or lower alkyl, and $R_6$ and $R_7$ are each selected from the group consisting of hydrogen, halogen, nitro, lower alkyl, phenyl, substituted phenyl, phenoxy, and lower alkoxy. The invention is also directed to photosensitive homopolymers containing the recurring unit:

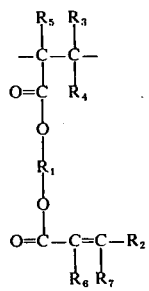

wherein $R_1$ is substituted or unsubstituted alkylene, aralkylene, alkoxyalkylene or aryloxyalkylene and $R_2$, $R_3$, $R_4$, $R_5$, $R_6$ and $R_7$ are as defined above. The invention is further directed to photosensitive substantially non-crosslinked (i.e., solvent soluble) copolymers containing said recurring unit and another recurring unit derived from an ethylenically unsaturated monomer. Also included in the invention are lithographic plates

4 bearing the aforementioned homopolymers and copolymers, as well as methods for preparing the monomers and polymers and for preparing and developing plates bearing these polymers. The monomers are prepared by reacting a first reactant represented by the general formulae:

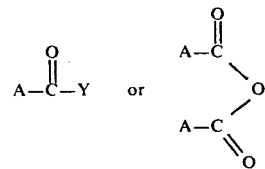

wherein A is selected from the group consisting of the groups having the general formulae:

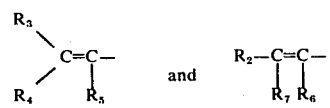

where $R_2$, $R_3$, $R_4$, $R_5$, $R_6$ and $R_7$ are as defined above and where Y is halogen or hydroxyl, with a second reactant represented by the general formula:

$$B-\overset{O}{\underset{\|}{C}}-O-R_1'-OH$$

where B is

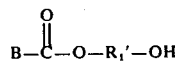

when A is

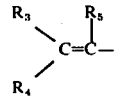

and B is

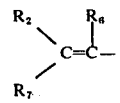

when A is

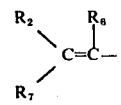

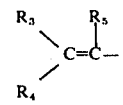

and $R_1'$ is as defined above, thereby producing said monomeric compound and a second product selected from the group consisting of compounds represented by the formulae:

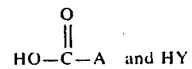

where A and Y are as defined above, and removing said compound represented by the formula HY from the reaction zone where HY is produced in order to promote the progress of the reaction. The homopolymers may be produced by preparing a mixture containing a monomer having the general formula

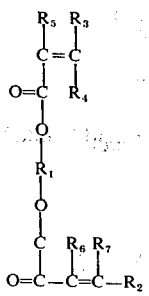

where $R_1$ is a substituted or unsubstituted alkylene, aralkylene, alkoxyalkylene or aryloxyalkylene group, and $R_2$, $R_3$, $R_4$, $R_5$, $R_6$, and $R_7$ are as defined above, and a polymerization initiator under an inert atmosphere; and holding said mixture under an inert atmosphere for a time sufficient for the polymer to form. The copolymers are produced by preparing a mixture containing one or more ethylenically unsaturated comonomers, a monomer of the same type as may be used to prepare the homopolymers, and a polymerization initiator under an inert atmosphere; and holding the resulting mixture under an inert atmosphere for a time sufficient for the polymer to form.

Lithographic plates are prepared according to this invention by preparing a solution or an emulsion comprising a volatile solvent and one of the photo-sensitive polymers of the invention; uniformly applying said solution to a surface of a base plate; and evaporating said solvent from the surface of the base plate. The resulting plate is prepared for printing by the additional steps of exposing the plate through a photographic negative to a source of actinic light for a time sufficient to photo-crosslink said photo-sensitive polymer in the areas exposed; and removing the non-crosslinked polymer from the unexposed areas of the plate with a solvent for the non-crosslinked polymer.

DESCRIPTION OF THE PREFERRED EMBODIMENTS

In accordance with the present invention, a presensitized lithographic plate is prepared which may be stored for extended periods of time without deterioration of the light-sensitive coating, by reaction with the substrate or otherwise. On exposure of this plate, a printing surface is generated which is highly adherent to its substrate and highly resistant to abrasion. As a result of its abrasion resistance and elasticity, this printing surface is capable of producing 200,000 to 1,000,000 good impressions without serious deterioration or wear. The novel soluble photopolymers which constitute the light-sensitive coating for these plates are readily prepared in high yield in accordance with the processes of the invention.

Though the invention is primarily directed to the provision of improved lithographic printing surfaces, those skilled in the art will recognize that the photopolymers of this invention can also be used in chemical milling, etching, the production of printed circuits and other related applications.

Each of the photopolymers of the invention has a linear backbone and a pendant diester moiety having a terminal group such as substituted or unsubstituted cinnamate, substituted or unsubstituted naphthyl acrylate, or substituted or unsubstituted anthracyl acrylate which serves as the crosslinking agent. The terminal crosslinking group may also be an acrylate substituted with a heterocyclic group having aromatic character. The heterocyclic group may itself be substituted or unsubstituted. In the absence of light, the polymers of this invention are quite stable and are soluble in a variety of organic solvents. On exposure to light, however, these polymers are quite readily photo-crosslinked through the carbon to carbon double bonds of the aryl acrylate or heterocyclic acrylate pendant groups.

Thus, as noted, each of the photopolymers of this invention contains the recurring unit:

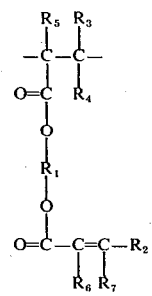

where $R_1$ is substituted or unsubstituted alkylene, aralkylene, alkoxyalkylene or aryloxyalkylene, and $R_2$, $R_3$, $R_4$, $R_5$, $R_6$ and $R_7$ are as defined above.

Exemplary linkages which may constitute $R_1$ include ethylene, propylene, butylene, isobutylene, isopropylene, octylene, hydroxybutylene, hydroxypropylene, dihydroxypropylene, phenylethylene, phenyloctylene, chloroethylene, bromobutylene, p-tolylbutylene, phenoxyethylene, p-nitrophenoxy propylene, ethoxypropylene, isopropoxypropylene, phenoxypropylene, 1-hydroxy, 3-phenoxy propylene, cyclohexylene, aminopropylene, cyanoethylene, cyclohexylpropylene and cyclopentylbutylene. Other linkages of these types, as will be apparent to those skilled in the art, are also within the scope of the invention.

Since each of the terminal groups of the pendant diester moieties is either a 1-aryl acrylate group or an acrylate group substituted with a heterocyclic group of aromatic character, $R_2$ is typically phenyl, naphthyl, anthracyl, nitrophenyl, dichlorophenyl, ethylphenyl, tolyl, 4-dodecylphenyl, nitrochlorophenyl, methoxyphenyl, 2,5-diethylphenyl, 3,4-xylyl, α-chloronaphthyl, β-bromonaphthyl, 2,6-dimethyl naphthyl, 1,8-dinitroanthra-9-cyl, 2-furyl, 2-thienyl, and 3-indolyl.

In the context of this disclosure, "lower alkyl" encompasses alkyl groups containing about 8 carbon atoms or less. Thus, typical groups which may constitute $R_3$ and $R_4$ in addition to hydrogen, include methyl, ethyl, n-propyl, heptyl, chlorine and bromine. $R_5$ may also be any of these latter groups. It is normally preferred, however, that $R_5$ not be hydrogen. If $R_5$ is hydrogen, it is necessarily a tertiary hydrogen and linear photopolymers occasionally tend to prematurely crosslink at tertiary hydrogens. For the same reason, it is generally preferable that $R_4$ be hydrogen only if $R_3$ is also, and vice-versa.

Typical groups which may constitute $R_6$ include methyl, ethyl, n-propyl, hexyl, nitro, phenyl, tolyl, phenoxy, ethoxy, methoxy, halogen and hydrogen. $R_7$ may be any of the groups that constitute $R_6$.

The photopolymers of this invention are preferably prepared either by homopolymerization of monomers having the general formula:

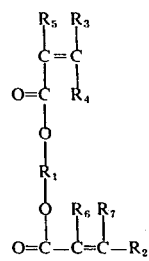

where $R_1$ through $R_7$ are as described above, or by copolymerization of such monomers with ethylenically unsaturated comonomers such as acrylic acid, methacrylic acid, maleic anhydride, styrene, dimethylaminoethyl methacrylate, tertiary-butylaminoethyl methacrylate, vinyl toluene, α-methyl styrene, dimethyl styrene, diethyl styrene, cyanostyrene, monochlorostyrene, dibromostyrene, difluorostyrene, trichlorostyrene, tetrabromostyrene, isopropenyl toluene, vinyl acetate, vinyl chloride, vinyl stearate, methyl methacrylate, butyl methacrylate, isopropyl methacrylate, methyl ethacrylate, ethyl methacrylate, ethyl ethacrylate, methyl acrylate, ethyl acrylate, isopropyl acrylate, butyl acrylate, vinylidene fluoride, methyl vinyl ether, ethyl vinyl ether, butyl vinyl ether, methly p-vinyl benzoate, ethyl p-vinyl benzoate, dimethyl fumarate, methyl ethyl fumarate, diethyl maleate, dimethyl itaconate, diethyl citraconate and paradimethyl amino styrene. Up to approximately 90 mole percent of the copolymer may be constituted by recurring units derived from ethylenically unsaturated comonomers. Exemplary copolymers are ethylene glycol methacrylate cinnamate (EGMC)/acrylic acid, propylene glycol methacrylate cinnamate (PGMC)/methacrylic acid, ethylene glycol acrylate cinnamate (EGAC)/methyl methacrylate, EGMC/dimethylaminoethyl methacrylate, PGMC/p-dimethylaminostyrene, EGMC/styrene/acrylic acid, EGMC/n-butyl acrylate/methacrylic acid and EGMC/styrene/methyl methacrylate/vinyl 2-pyrrolidone.

Alternative methods of producing the photopolymers of the invention will occur to those skilled in the art. It is preferred, however, that the monomeric diester be prepared first. Most of such monomeric diesters are also novel compounds which are uniquely adapted for the preparation of the photopolymers of the invention. We have found that novel monomers are prepared by reacting certain hydroxy esters having the general formula:

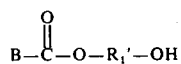

where B is a group having the general formula:

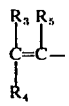

or

with a carboxylic acid or acid halide having the general formula:

or an acid anhydride having the formula:

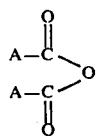

where Y is halogen or hydroxyl and A is:

when B is:

and A is:

when B is

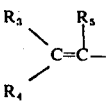

$R_1'$, $R_2$, $R_3$, $R_4$, $R_5$, $R_6$ and $R_7$ being as defined above.
The products of these reactions are generally the desired diester monomers and either water or a hydrogen halide. Where greater than an equivalent of an anhydride per equivalent of hydroxyester is present, the acid

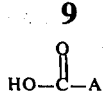

is also a reaction product. These reactions are reversible and it is necessary to remove water or hydrogen halide from the reaction zone in order to drive the reaction to completion. The latter result may be accomplished either by distilling the water or hydrogen halide from the reaction mixture or, as may be particulary convenient in the case of a hydrogen halide, scavenging this by-product material with an acceptor therefor.

Conveniently, an acid halide such as cinnamoyl chloride; m-nitro cinnamoyl chloride; methoxy cinnamoyl bromide; 1-anthracyl acryloyl bromide; or 3-indolyl acryloyl chloride is reacted with a hydroxyester such as 2-hydroxybutyl 1-acrylate; 3-hydroxybutyl 2-acrylate; 3-chloro,2-hydroxypropyl crotonate; 3-bromo, 2-hydroxypropyl 2-chloroacrylate; 2-hydroxypropyl 3-chloroacrylate; 2-hydroxy, 3-p-nitrophenoxypropyl 2,3-dichloroacrylate; 2-hydroxy, 3-isopropoxypropyl 3,3-dichloroacrylate; 2-hydroxy, 3-phenoxypropyl trichloroacrylate; 2-hydroxy, 2-phenylethyl α-bromoacrylate and 2-hydroxycyclohexyl α-ethacrylate.

Since the use of heat as well as an acid or basic catalyst is generally required for esterification to proceed at a satisfactory rate with an acid or acid anhydride, the use of an acid halide is preferred in the monomer synthesis. A variety of hydrogen halide acceptors may be employed in synthesizing the monomer from an acid halide. In general, almost any base can be employed for this purpose. Where inorganic bases such as potassium hydroxide or sodium hydroxide are employed, the reaction follows the classical SchottenBaumann mechanism but, unlike most Schotten-Baumann syntheses, the monomer formation reactions of this invention proceed more satisfactorily in the absence of water. Among the organic bases which may serve as the hydrogen halide acceptor, the tertiary amines are preferred since they react rapidly with hydrogen halides to produce insoluble adducts which precipitate from the reaction medium. The tertiary amines, moreover, can be readily reclaimed from their hydrogen halide adducts by reaction with an alkali metal hydroxide and then recycled to the reaction zone. Pyridine has been found to be a particularly useful hydrogen halide acceptor for the reactions of this invention. It is preferable to have a slight molar excess, e.g., 2–3% excess, of the halide acceptor present in the reaction solution.

The monomer formation reaction may be carried out in bulk. Preferably, however, this reaction is carried out in an organic solvent. An extremely wide range of organic solvents can be used. In fact, essentially any organic solvent that does not react with hydroxyesters, carboxylic acids, acid anhydrides or acid halides can be utilized. It is generally preferable to employ a solvent having a somewhat higher vapor pressure than the diester monomer to facilitate recovery of the monomer from the reaction solution. Most organic solvents satisfy this criterion. Among the numerous useful solvents may be mentioned benzene, toluene, xylene, ethyl ether, ethyl amyl ether, ethyl butyl ether, ethyl isopropyl ether, dipropyl ether, dibutyl ether, methyl ethyl ketone, diethyl ketone, methyl isopropyl ketone, methyl isobutyl ketone, methyl isoamyl ketone, ethyl isopropyl ketone, methylene dichloride, ethylene dichloride, perchloroethylene, and o-dichlorobenzene.

Benzene and toluene have proved to be particularly desirable solvents for the monomer formation reaction and, since these solvents are also well adapted for the polymerization reaction, it is often convenient to conduct the monomer formation reaction in such solvents as these and then proceed with the polymerization reaction without recovery of the monomer.

To avoid excessive loss or recycle of raw materials, it is normally desirable to utilize essentially equimolar quantitites of reactants. In a preferred embodiment of the invention, the hydroxyester is initially dissolved in the bulk of a solvent, and a solution of the carboxylic acid, acid halide or acid anhydride is added dropwise to the hydroxyester solution over a period of 30–60 minutes while stirring the mixture. Where an acid halide is used, a hydrogen halide acceptor such as a tertiary amine is initially incorporated in the hydroxyester solution. Preferably, sufficient solvent is used so that the monomer reaction mixture is sufficiently fluid that it may be stirred easily. Normally the concentration of monomer after completion of the reaction is approximately 50–70% by weight.

The temperature of the monomer formation reaction is preferably maintained below about 70°C. in order to prevent premature polymerization. Temperatures above 70°C. can be tolerated if a polymerization inhibitor is used but fully satisfactory reaction rates are obtained at temperatures below 70°C. The preferred temperature of the monomer formation reaction is between about 0°–60°C., although the reaction will proceed reasonably satisfactorily at even lower temperatures. This reaction is exothermic and heat removal is necessary if isothermal conditions are to be maintained. Where volatile solvents are used, the reaction system is maintained under reflux and at least part of the heat removal is accomplished thereby.

After completion of the reaction, the monomer may be recovered from the reaction mixture by conventional separation procedures well-known to the art. Conveniently, the solvent is merely stripped off. Where a hydrogen halide acceptor which yields an insoluble by-product is used, this by-product is initially separated from the reaction mixture by conventional solid/liquid separation means, as by filtration. To insure maxiumum product recovery, the filter cake is preferably washed with solvent and the washings added to the filtrate.

It is generally desirable to wash the reaction mixture with dilute alkaline solution before solvent removal to insure the elimination of residual amounts of acidic reaction by-products. If one of the reactants is an acid halide, any halide acceptor adduct precipitate present is filtered off prior to washing the reaction solution. The dilute alkaline wash is followed with a dilute acid wash to neutralize residual alkalinity resulting from the alkaline wash or from alkaline reaction by-products. The acid wash is followed with a water wash to remove acid and salts. The resulting monomer solution is dehydrated and preferably decolorized with activated carbon before the solvent is stripped off. To prevent premature polymerization during the monomer recovery operation, it is preferable to add a small proportion of a polymerization inhibitor such as hydroquinone, t-butylcatechol or methoxyhydroquinone.

Two monomers, the homopolymers and copolymers of which have been found to be especially effective photopolymers, are ethylene glycol methacrylate cinnamate and propylene glycol methacrylate cinnamate. In the preferred embodiments of this invention, these monomers are prepared by the reaction of cinnamoyl chloride with hydroxyethyl methacrylate and hydroxypropyl methacrylate, respectively. The substantially non-crosslinked polymers prepared from these monomers are quite stable under normal conditions but are readily photo-crosslinked under the influence of actinic light to produce hardened insoluble oleophilic materials which are highly adherent to the substrate and highly resistant to abrasion and are thus uniquely adapted for use as lithographic printing surfaces.

In the preparation of ethylene glycol methacrylate cinnamate (hereinafter referred to as EGMC) and propylene glycol methacrylate cinnamate (hereinafter referred to as PGMC), the yield and quality of the monomer may be improved by using purified raw materials. Commercial cinnamoyl chloride may be purified by vacuum distillation followed by crystallization from petroleum ether. Hydroxyethyl methacrylate and hydroxypropyl methacrylate may be purified by distillation at very low pressure, less than 1 torr, at a low temperature differential in the presence of about 1% by weight para-tertiary butylcatechol as a polymerization inhibitor.

Cinnamic anhydride is commonly a byproduct of EGMC or PGMC synthesis from cinnamoyl chloride and wet hydroxyalkyl methacrylate, even where otherwise pure raw materials are used. Up to about 25% by weight cinnamic anhydride can be tolerated in the monomer without having adverse effect on polymers prepared therefrom. If dry hydroxyalkyl methacrylate is used in preparing the monomer, however, by-product cinnamic anhydride generation is substantially avoided. Such cinnamic anhydride as may be formed should be removed in washing the reaction mixture.

The photopolymers of this invention may be produced by either solution, emulsion, suspension or bulk polymerization. In the preparation of photopolymers for lithographic use, solution polymerization is preferred. Polymerization conditions are controlled so that the polymer produced is substantially noncrosslinked and, therefore, soluble in common organic solvents. A certain degree of chain branching can be tolerated without adversely affecting the properties of the photopolymers but substantial crosslinking must be avoided. Preferably the photopolymer has a solubility on the order of 95–100% in vehicles such as chloroform and ethylene glycol monomethyl ether acetate which are useful for plate coating. If solubility is too low, difficulties may be encountered in obtaining uniform plate coatings and the plate may be subject to scumming after development due to residual polymer which is not removed from the unexposed areas of the plate by the developing solvent.

Where the process schemes of the present invention are followed, unlike certain previously known processes for producing photopolymers, substantial crosslinking is avoided without serious difficulty. Certain ranges of conditions are required or preferred, however, and these are described in detail below.

Solution polymerization is accomplished by preparing a mixture containing the monomer(s), a polymerization initiator and an organic solvent, and holding this mixture at elevated temperatures for a time sufficient for the polymer to form. The polymerization reaction should be conducted under an inert atmosphere to exclude oxygen. Oxygen is a free radical scavenger which inhibits the progress of polymerization. An inert atmosphere may be provided by means of a blanket of inert gas under positive pressure or by polymerizing at a temperature at which the vapor pressure of the polymerization mixture equals the total pressure of the system, e.g., under reflux conditions.

A wide range of temperatures may be employed for solution polymerization but a temperature of between about 60°–80°C. has been found to be optimum. At temperatures in this range, polymerization proceeds to a conversion of 25–50% in 3–5 hours, 50–75% in 10–12 hours and up to 85–90% in 15–20 hours. Termination of the reaction after periods of anywhere from 3–48 hours normally results in the production of fully satisfactory photopolymers. However, not only the yields but also the molecular weight of these polymers and, in the case of copolymers, the tendency for excessive premature crosslinking, are functions of the polymerization reaction period. Thus, if a very short polymerization time is allowed, for example 2–4 hours, a relatively low molecular weight polymer is sometimes formed, which may not always be photo-crosslinkable into a printing surface of sufficient hardness. Exceptionally long polymerization times, on the other hand, while providing maximum yields, can occasionally result in the formation of a gelled product. The polymerization time which provides the optimum balance between yield and product quality varies. For many polymerization systems, optimum results are obtained at a temperature of approximately 70°C. for a period of about 10–12 hours. However, for a toluene solvent system containing 15 g. monomer per 85 ml. solvent, for example, the optimum polymerization time is on the order of 24 hours.

Essentially any of the numerous polymerization initiators may be utilized in the polymerization reaction. Particularly useful initiators include azides such as azobisisobutyronitrile, azodicyclohexylcarbonitrile and dimethyl $\alpha$, $\alpha'$ azodiisobutyrate and the organic peroxides such as benzoyl peroxide, lauroyl peroxide, cumene hydroperoxide, dicumyl peroxide, dichlorobenzoyl peroxide and t-butyl hydroperoxide. Concentrations up to 5% by weight of the initiator can be employed.

Wide latitude exists with regard to the choice of solvent for solution polymerization. Almost any of the solvents mentioned above as useful for the monomer formation reaction may also be employed in the polymerization reaction. Generally, the solvent which is used should be inert to the reaction and should be a solvent for both the monomers and polymer product. The latter criterion would normally exclude alcohols. However, in certain circumstances, it may be advantageous to recover the polymer as a precipitated product and in this instance an alcohol solvent is actually preferred. But in most cases, a solvent such as xylene, toluene, benzene or methylene dichloride is preferred and, as indicated above, it is often convenient to employ the same solvent for both the monomer formation and polymerization reactions and bypass recovery of the monomer from its reaction solution.

The preferred initial monomer concentration in the polymerization medium varies sharply among solvents. Productivity, yield and the molecular weight of the polymer are increased by using higher concentrations, but if the concentration rises too high, gelation can result. Thus, when polymerization is carried out in toluene or xylene, the monomer concentration is preferably between about 15 g./85 ml. solvent and about 20 g./80 ml. solvent. Where a chlorinated solvent such as trichloroethylene is used, the initial monomer concentration is preferably on the order of 30 g./70 ml. solvent to 40 g./60 ml. solvent. The proper concentrations to be used with any particular solvent may be readily determined by simple testing methods which are well known to those skilled in the art.

The finished photopolymer is recovered from the polymerization reaction mixture by any convenient method, e.g., by simply stripping off the solvent. A preferred method of recovery is to mix the polymerization reaction solution with a large excess of a low molecular weight alcohol, thus precipitating out the polymer which is then recovered by filtration.

Emulsion polymerization can generally be conducted at much faster rates than solution polymerization, though control of product quality may, in some cases, be more difficult. In this polymerization method, an emulsion of monomer in water is prepared and a water-soluble initiator is added to the emulsion. The initiator is activated either by heating the system to its reflux temperature of about 90°–95°C. (the "reflux" method) or by incorporating a reducing agent in the system (the "redox" method). Either of these techniques generates free radicals from the initiator which in turn attack the monomer and start the chain reaction of polymerization.

In either the reflux or redox method, the emulsion typically contains between 20% and 40% by weight of monomer based on the weight of the emulsion and between about 0.1% and 2% of water soluble initiator based on the weight of the monomer. Approximately 1–6% by weight of any emulsifying agent, based on the monomer, is required to produce the degree of dispersion required to form an emulsion. As indicated above, the temperature of reaction in the reflux process is typically 90°–95°C. The redox process does not require elevated temperatures and is conveniently conducted at temperatures between room temperature and 60°C. An inert atmosphere is maintained above the reaction mixture during polymerization. In the reflux method, the vapor pressure of the system equals the total pressure and oxygen is excluded without an independent inert gas supply. In the redox method, an independent inert gas supply is necessary. Reaction time, for both methods, is 1–2 hours.

Among the water-soluble initiators which are employed in emulsion polymerization may be noted ammonium persulfate, sodium persulfate, potassium persulfate, tertiarybutyl hydroperoxide and hydrogen peroxide. The emulsifying agent may be essentially any ionic or non-ionic surfactant which is compatible with the monomers employed. Most monomers are compatible with most surfactants but there are some combinations which do not yield satisfactory emulsions. The compatibility or incompatibility of various monomer-surfactant combinations may be determined by simple testing.

In the redox method, the reducing agent which acts directly on the initiator is conveniently a metal ion, such as ferrous or cerous ion, which has a higher oxidation state to which it is converted on reaction with the initiator. In a preferred embodiment of the invention, only a catalytic amount of the metal ion is present and a relatively large amount, for example 0.1 to 2% by weight based on the monomer, of another reducing agent is employed for purposes of reducing oxidized ions such as ferric ions back to ferrous for further reaction with the initiator. Among the secondary reducing agents which may be so employed are sodium formaldehyde sulfoxylate, sodium sulfite, sodium metabisulfite, sodium hydrosulfite and sodium thiosulfate.

After completion of the polymerization reaction, the polymer is conveniently recovered from the emulsion by addition of an excess of a lower alcohol and the resulting precipitate separated from the mixture by filtration. Alternatively, the polymer may be recovered by precipitation through acidification of the emulsion or by destroying the emulsion through addition of a salt such as sodium chloride. Other methods of recovering the polymer from the emulsion will be apparent to those skilled in the art.

The techniques employed in suspension polymerization are in certain ways similar to those employed in emulsion polymerization, but the nature of the process is quite different. Thus, suspension polymerization, like emulsion polymerization, utilizes an aqueous carrier for the monomer and includes similar types of surfactants in the reaction system. However, the surfactant is employed in smaller proportions and thus acts not as an emulsifier but as a dispersing agent which aids the breakdown of the bulk of monomer into small globules distributed throughout the aqueous medium. A solvent-soluble initiator is used so that each monomer globule is essentially a bulk polymerization site. As the polymerization reaction progresses, solid polymer particles are precipitated and, if the system is not strongly agitated, may settle out at the bottom of the polymerization vessel.

To prevent agglomeration of globules of partially polymerized material, a suspending agent, thickener or salt is usually incorporated in the polymerization medium. Colloidal suspending agents such as cellulose derivatives, gums, polyacrylate salts, gelatin, starch, alginates and polyvinyl alcohol are absorbed on the surface of the globules and prevent their sticking together. Thickeners, such as glycols, glycerol, and polyglycols increase the viscosity of the system, and thus its degree of dispersion. Salts increase interfacial tension, lower the solubility of the monomer in the aqueous phase and increase its density.

A small amount of a lubricant such as lauryl alcohol, cetyl alcohol or stearic acid is also preferably included in the polymerization medium. Lubricants promote the formation of uniform globules of polymerizing material.

The proportions of monomer and initiator are approximately the same for a suspension polymerization system as they are for an emulsion system. Polymerization is conveniently conducted at temperatures on the order of about 70° to about 90°C. under an inert atmosphere. Product recovery is effected by filtration of the solid polymer product from the water carrier.

Bulk polymerization is carried out by simply adding an initiator to a monomer or monomer mixture. A solvent-soluble initiator is used and, as soon as it is added to the monomer, polymerization commences at room temperature. Since addition polymerization reactions are highly exothermic, it is preferable that the temperature by maintained around room temperature or lower throughout the reaction. In any case, the temperature should be kept below 50°C., since at higher temperatures, a runaway reaction may occur. At room temperature, the polymerization reaction typically proceeds to 100% conversion in approximately 24 hours. During the reaction, the system is maintained under an inert atmosphere to prevent interference with operation of the initiator and should be stirred to provide uniform distribution of reactant and to assist in heat transfer.

The lithographic plates of the invention are prepared by applying a dilute solution or emulsion of photopolymer in a volatile solvent to the surface of a base plate. Here again, a wide variety of solvents may be used. Thus, aromatic hydrocarbons, halogenated solvents, esters, ethers and ketones are generally effective. A particularly effective vehicle for the photopolymers is a 50–50 weight-to-weight mixture of ethylene glycol monoethyl ether acetate and methyl ethyl ketone.

The concentration of photopolymer in the application vehicle may vary widely depending upon the method of coating. If whirl coating is employed, the polymer concentration should not normally exceed about 5% by weight, or an excessively thick layer of polymer may be formed which requires an extended exposure time for satisfactory development. Higher concentrations of polymer can be used, however, if rod or roller coating is employed. For roller coating, the polymer concentration may be on the order of 70% or higher by weight. Other methods which may be employed include simply wiping the polymer solution on the plate with a brush or cloth, spray coating, and curtain coating. The appropriate polymer concentrations best adapted to each of these methods can be readily determined by simple experimentation.

Although the photopolymers of this invention readily crosslink on exposure to ultraviolet light of an appropriately short wave length, a sensitizer is preferably included in the light-sensitive coating so that it crosslinks at the longer wave lengths emitted by carbon arc or pulsed xenon ultraviolet light sources. 4-4' bis (diethylamino) benzophenone (DEAB), in a concentration of about 5 parts per 95 parts photopolymer, is the preferred sensitizer. Other useful sensitizers include 4-4' bis (dimethylamino) benzophenone, benzil, anthraquinone, and thiazole.

The linear photopolymers of the invention may be applied to any of the various base plates which are conventionally used in the lithographic art to produce the lithographic plates of the invention. Among the various base plates which may be employed are those wherein the substrate for the photopolymer is constituted by aluminum, zinc, magnesium, plastic or paper. Where an aluminum base plate (currently the most prevalent type of base plate in the art) is used as a substrate for the photopolymer, the plate is preferably subjected to certain pre-treatment operations before receiving the photopolymer coating in order to insure the production of a rugged plate which will provide sharp and clear printed images.

The initial step of pre-treatment simply involves cleaning and degreasing of the plate. Cleaning and degreasing may be accomplished by use of any suitable solvent, for example, isopropanol. A preferred method of degreasing the substrate is to immerse it in a solution containing 1% trisodium phosphate and 1% sodium metasilicate at a temperature of about 150°F. for a period of about one minute.

After degreasing and cleaning, the substrate is grained. Graining may be accomplished by various methods which involve either mechanical, chemical or electrochemical action. Mechanical graining is effected by use of any suitable abrading technique such as, for example, sandblasting, ball graining or brush graining. The substrate may be chemically grained by immersion in a mixture of phosphoric and hydrofluoric acids, such as for example, a solution containing about 30 parts water, about 7 parts 85% phosphoric acid and about 0.03 parts hydrofluoric acid. Various caustic solutions may also be employed, as may dilute hydrofluoric acid if the operation is carefully controlled. A convenient method of electrochemical graining is described by Wruck in U.S. Pat. No. 3,072,546. In accordance with this method, two plates to be grained are immersed in a weak hydrochloric acid solution having a strength of about ½ Be to about 1 Be, the two plates being disposed in parallel facing relation between about ¾ inch and about 1⅛ inch apart. An alternating current is then passed between the two opposed surfaces at a voltage between about 5 and about 11 volts, at a temperature between about 15° and 26°C. for a period of 25 to 35 minutes. Other useful electrochemical graining methods are described in Hering U.S. Pat. No. 2,687,373 and Adams U.S. Pat. No. 3,073,765.

Following graining, the aluminum substrate is preferably anodized. Anodization of the substrate helps give the photopolymer "feet", i.e., it promotes adherence of the photocross-linked polymer to the plate following exposure. In a preferred embodiment of the invention, the substrate is anodized in a sulfuric acid solution containing 10–50% by weight $H_2SO_4$ at approximately room temperature using alternating current at a density of 15–25 amperes per square foot. Anodization can also be accomplished in a phosphoric acid solution having a strength between about 25% and 35% by weight, preferably using direct current, at a current density of between about 4 and 22.7 amperes per square foot and a temperature of between about 70° and about 120°F. A time of between about three-fourths of a minute and six minutes is usually required, for example, to properly anodize the surface of a grained aluminum substrate. Other reasonably well dissociated organic or inorganic acids such as, for example, hydrochloric, chromic, oxalic and citric acid may be used in anodizing the substrate, under conditions similar to those stated above for phosphoric and sulfuric acids. The anodized substrate is then washed thoroughly with water to remove the acid electrolyte and the excess water is removed from the washed, anodized sheet, preferably by suitable mechanical means such as, for example, squeegeeing.

To promote releasability of unexposed photopolymer from the surface of the base plate following exposure and to insure the hydrophilicity of the surface, the base plate preferably includes a "barrier" layer overlying the aluminum substrate. This barrier layer, which may conveniently be constituted by an alkali metal silicate, a polyacrylic acid or any of the other materials described in the patents referred to above, is thus interposed between the surface of the substrate and the photopolymer coating. The extent of direct contact between the photopolymer and the aluminum substrate is thereby minimized. This obviates difficulties which can occasionally arise as a result of a tendency of the photopolymer to strongly adhere to the aluminum substrate and resist removal on development. While it thus promotes removal of unexposed polymer during development, the use of a barrier layer does not have a significant adverse effect on adhesion of the photo-hardened polymer, particularly if the substrate is anodized.

A silicate barrier layer may be applied to an aluminum substrate by any of the various conventional methods known to the art. Among such methods are those described in U.S. Pat. No. 2,714,066 and U.S. Pat. No. 3,181,461.

To apply a polyacrylic acid barrier layer, the aluminum substrate is contacted at room temperature with an aqueous solution of colloidal polyacrylic acid having a molecular weight of between about 30,000 and about 300,000. Such solutions are commercially available, including, for example, the various polyacrylic acid solutions sold under the trade name "Acrysol" by Rohm & Haas Company. Thus, "Acrysol A-3" contains 25% by weight polyacrylic acid having a molecular weight of less than 150,000, and "Acrysol A-5" contains 25% by weight polyacrylic acid having a molecular weight of less than 300,000. It will be understood that other commercially available polyacrylic acid solutions may also be used. The strength of the polyacrylic acid solution as applied should not be higher than about 5% by weight and, if the above noted "Acrysols" are used, they should be diluted to this strength or lower. Contact of the surface with the substrate can be any convenient means, such as by brief immersion, spraying, et cetera.

After the surface of the substrate is fully coated with polyacrylic acid solution, excess solution is removed, as by squeegeeing. The plate is then dried, which may be accomplished by simply allowing moisture to evaporate therefrom. Alternatively, heat, forced air or vacuum may be employed to accelerate drying.

The preferred base plate of the invention is constituted by an electrochemically grained and anodized aluminum sheet, to which a barrier layer may optionally be applied.

The lithographic plates of this invention are prepared for printing by exposing them to a source of actinic light through a photographic negative and developing the exposed plate with a solvent for the unexposed photopolymer. The degree of exposure required to fully photoharden the polymer in the exposed area is on the order of 20 lux units or higher. Since the photopolymers of this invention form insoluble films when photocrosslinked, they may be developed simply by use of an organic solvent. The use of emulsion developers which are required for conventional diazo resins in order to provide a lacquer film on the exterior surface of the exposed resin is not necessary for the development of the photopolymers of this invention, but such developers may be employed. A developing solvent which has been found especially suitable for the lithographic plates of this invention is ethylene glycol monoethyl ether acetate which may be employed either by itself or in emulsion form.

The following examples illustrate the invention.

EXAMPLE 1

A solution of cinnamoyl chloride (175 g.) in methylene chloride (300 ml.) was slowly added to an ice bath chilled solution of 2-hydroxyethyl methacrylate (130 g.) and triethyl amine (106 g.) in methylene chloride (200 ml.). After addition was complete, the mixture was allowed to come to room temperature by absorption of exothermic heat of reaction and was then refluxed on a steam bath for 15 minutes. The reaction mixture was cooled and a triethyl amine hydrochloride precipitate, which formed during the reaction, was filtered off. The filtrate was washed several times with a dilute sodium bicarbonate solution, then with dilute HCl and finally with water. The methylene chloride solvent was stripped from the filtrate and a viscous yellow liquid (230 g.) was recovered and identified as ethylene glycol methacrylate cinnamate by I.R. and elemental analyses.

EXAMPLE 2

Purified hydroxyethyl methacrylate was prepared by distilling a mixture containing crude hydroxyethyl methacrylate and approximately 1% by weight p-t-butylcatechol at an absolute pressure of less than 1 torr and a temperature of 60°–65°C. Cinnamoyl chloride was purified by vacuum distillation through a one-foot Vigreaux column followed by recrystallization from petroleum ether.

To a mixture of hydroxyethyl methacrylate (141 g.), pyridine (83 g.), and toluene (200 ml.), a solution of cinnamoyl chloride (166.6 g.) in toluene (300 ml.) was added dropwise over a period of one hour. The reaction mixture was stirred continuously and a positive pressure of dry argon was maintained over the mixture to exclude moisture. The reaction temperature was held at 50°C. to 60°C. When addition of cinnamoyl chloride was complete, the reaction mixture was a thick white slurry. Stirring with heating was continued for 45 minutes. Then the mixture was cooled rapidly to room temperature and filtered through a coarse sintered glass frit. The filter cake, pyridine hydrochloride, was washed once with boiling toluene, then dried and weighed. 110 g. of pyridine hydrochloride were recovered, 95% of theoretical.

The filtrate was washed twice with dilute aqueous potassium carbonate, twice with distilled water, twice with dilute aqueous hydrochloric acid, and then with water until neutral to litmus paper. The washed filtrate was dried with anhydrous sodium sulfate, then with calcium sulfate after which it was treated with an activated carbon sold under the trade designation "Norit A" by the American Norit Company. After drying and carbon treatment, the filtrate was subjected to a final filtration through a medium porosity frit yielding a clear solution having a faint yellow color. Hydroquinone (0.5 g.) was then added to inhibit polymerization and the toluene solvent was stripped off using a rotary evaporator. 246 g. of a slightly translucent, pale yellow, viscous liquid identified as ethylene glycol methacrylate cinnamate was recovered.

EXAMPLE 3

Freshly distilled hydroxyethyl methacrylate (1 mole) was dissolved in dry ether (650 ml.) and pyridine (1.05 moles) was added to the solution. Cinnamoyl chloride (1 mole) dissolved in dry ether (200 ml.) was added to the hydroxyethyl methacrylate solution over a period of 45 minutes while the solution was stirred vigorously. A mildly exothermic reaction took place producing a thick yellow slurry which was stirred overnight to insure complete reaction. This slurry was then filtered and the filter cake washed three times with ether leaving 113.4 g. of pyridine hydrochloride (98.2% of theoretical).

The filtrate was washed successively with dilute sodium hydroxide, water, dilute HCl and once again with water until neutral, then dried overnight over a mixture of anhydrous sodium and calcium sulfates. Hydroquinone (0.025 g.) was added to inhibit polymerization and the ether solvent stripped off at 30° to 40°C. in a rotary evaporator. 248 g. of a viscous pale yellow liquid identified as ethylene glycol methacrylate cinnamate was recovered.

EXAMPLE 4

A solution of cinnamoyl chloride (66.6 g.) in diethyl ether (100 ml.) was added dropwise to a solution of hydroxypropyl methacrylate (57.3 g.) and dry pyridine (33.2 g.) in diethyl ether (100 ml.). The reaction mixture was stirred vigorously during addition of the cinnamoyl chloride solution, which was completed in 45 minutes. As the reaction proceeded, a thick yellow slurry formed in the reaction vessel. This slurry was stirred at ambient temperature overnight and then filtered. The filter cake was washed three times with dry diethyl ether and then dried yielding 47.5 g. of pyridine hydrochloride (98% of theoretical). The filter cake washings were combined with the filtrate and washed with dilute aqueous sodium hydroxide, distilled water, dilute aqueous HCl, and again with distilled water to neutrality. The washed filtrate solution was dried overnight over a mixture of anhydrous sodium sulfate and calcium sulfate. Hydroquinone (0.15 g.) was added to the dried filtrate and the solvent diethyl ether stripped off in a rotary evaporator at 30° to 40°C. yielding 96 g. of a bright yellow viscous liquid identified as propylene glycol methacrylate cinnamate.

EXAMPLE 5

A solution was prepared containing 30.0 g. of EGMC (prepared according to the method described in Example 2) in benzene (170 ml.). Azobis isobutyronitrile (AIBN) (0.0945 g.) was added to the solution and the resulting mixture held at 70°C. for 3 hours in a closed, argon purged, tumbling polymerization vessel. The solution was then transferred to a Waring blender containing a 20-fold excess of methanol whereupon a precipitate of polymeric EGMC began to form. The precipitated polymer was allowed to settle for 30 minutes, the supernatant liquid was decanted and methanol (350 ml.) was poured onto the slightly tacky polymer mass. Then the polymer was broken into small fragments with a spatula, placed back in the Waring blender and agitated for 10 to 15 seconds. After this, the polymer was filtered on a medium porosity sintered glass funnel, again recycled to the blender, again agitated for 10 to 15 seconds and then refiltered. The resulting filter cake was crushed with a spatula, then air dried in subdued light yielding a free-flowing clear white powder. 13.6 g. of powdered EGMC polymer was recovered.

A 4% solution of this polymer in chloroform with 0.2% DEAB was applied with a wire draw-down rod to the surface of an aluminum base plate which had initially been electrochemically grained, anodized, and provided with a silicate barrier layer. After the chloroform solvent had evaporated and the plate was fully dried it was exposed to 20 luxometer units of actinic light through a photographic negative. The exposed plate was developed by application of ethylene glycol monoethyl ether acetate to remove the unexposed polymer. The resulting plate was highly abrasion resistant and provided 80,000 good impressions during printing tests.

EXAMPLE 6

To a slurry of sodium hydroxide pellets (10 g.) in hydroxyethyl methacrylate (100 g.), a solution of cinnamoyl chloride (34 g.) in toluene (50 ml.) was slowly added over a one hour period while the resulting mixture was stirred at 50°C. The solution was cooled to room temperature and poured into deionized water (400 ml.) and stirred for 15 minutes. The aqueous layer was drained and the organic layer washed successively with two 300 ml. portions of 10% aqueous sodium carbonate, two 300 ml. portions of deionized water, two 300 ml. portions of 1N hydrochloric acid, and finally with three portions of 300 ml. of deionized water, the final wash being neutral to litmus. The solution was diluted with toluene (200 ml.) and dried with anhydrous sodium sulfate (20 g.).

EXAMPLE 7

A solution of cinnamoyl chloride (1.50 moles) in methylene chloride (400 ml.) was added dropwise to a solution of hydroxypropyl methacrylate (1.53 moles) and triethylamine (1.60 moles) in methylene chloride (300 ml.). The reaction mixture was stirred continuously during the cinnamoyl chloride addition and cooled with an ice water bath. The reaction product was recovered in the manner described in Example 4, yielding 385 g. (94% of theoretical) of a pale viscous liquid identified as propylene glycol methacrylate cinnamate.

EXAMPLE 8

A first reactant solution was prepared consisting of hydroxyethyl methacrylate (705 g.) and pyridine (410 g.) in benzene (400 ml.). A second reactant solution consisting of cinnamoyl chloride (835 g.) in benzene (600 ml.) was added slowly to the first reactant solution over a two hour period, the reaction vessel being cooled externally in an ice water bath and purged internally with dry nitrogen. After addition of the cinnamoyl chloride solution was complete, the resulting yellow viscous slurry was stirred for another 2 hours at room temperature. The slurry was then filtered through a coarse sintered glass frit and the pyridine hydrochloride filter cake washed with hot benzene (200 ml.). The filtrate was washed successively with two 1500 ml. portions of 5% sodium carbonate solution, two 1500 ml. portions of 5% hydrochloric acid solution, and three 1500 ml. portions of deionized water. The washed filtrate was dehydrated with calcium chloride (200 g.) and then with anhydrous sodium sulfate (200 g.). 2.5 g. of p-tertiary butyl catechol were added and the benzene solvent stripped off on a rotary vacuum evaporator at 40°C., yielding a yellow oil (1225 g.) identified as ethylene glycol methacrylate cinnamate.

EXAMPLE 9

Hydroxypropyl methacrylate (781 g.) was reacted with cinnamoyl chloride (835 g.) in the manner and under the conditions described in Example 8. Recovery of the product was also conducted in the manner described in Example 8, yielding 1293 g. of a yellow oily monomer identifed as propylene glycol methacrylate cinnamate.

EXAMPLE 10

A mixture of methacrylic acid (86.1 g.) and styrene oxide (60.1 g.) was prepared in a 500 ml., one neck, round bottom flask. To this mixture was added a 40% by weight solution of benzyltrimethyl ammonium hydroxide in methanol (21 g. solution, 8.4 g. "active" catalyst). The initially clear, colorless solution was protected from the atmosphere with a tube of anhydrous calcium sulfate and was stirred magnetically for 94 hours using a Teflon coated stir bar. The solution remained clear throughout the reaction, coloring to a bright greenish-yellow near the end of the reaction period. The progress of the reaction was followed by monitoring the disappearance of the characteristic I.R. epoxide absorption of styrene oxide at 871 cm$^{-1}$. This absorption peak was about half gone after 20 hours, indicating this time as the half life of the reaction, and after 94 hours this peak was completely absent. The product was recovered by adding 0.50 moles of NaOH dissolved in 200 ml. of distilled water and shaking the mixture vigorously to form the sodium salt of methacrylic acid. After a few minutes, the resulting yellow emulsion was shaken with 300 ml. diethyl ether and the aqueous layer discarded, thus removing excess methacrylic acid from the mixture in the form of its sodium salt. The ether layer was sequentially washed with a solution of 2 g. NaOH in 100 ml. distilled water, then five times with distilled water. The washed solution was dried over anhydrous calcium sulfate and the ether solvent stripped off in a rotary evaporator at room temperature after a pinch of hydroquinone was added to prevent polymerization. The I.R. spectrum of this product was fully consistent with that expected, showing a strong OH absorption at 2.9 microns, ester carbonyl at 5.85 microns and a mono-substituted phenyl bond pattern at 13.2 and 14.3 microns. The product was thus identified as a $\alpha$- and $\beta$-phenylhydroxyethyl methacrylate.

To 75 g. of the above product in a 250 ml., three neck, round bottom flask were added dry pyridine (28.4 g.) and 100 ml. diethyl ether. Cinnamoyl chloride (60.5 g) in 100 ml. diethyl ether was added dropwise to the rapidly stirred reaction mixture over a period of 1 ½ hours. The resultant yellow slurry was stirred overnight and the product recovered by the method described in Example 8.

An extremely viscous yellow liquid (103 g.) having the expected cinnamoyl ester I.R. spectrum was obtained. The strong OH bond at 2.9 microns was almost entirely gone from the spectrum.

EXAMPLE 11

60 g. of the EGMC monomer prepared in Example 2 was charged into a 500 ml. three necked flask with benzene (350 ml.) and 0.26 g. of 2,2'-azobis (2-methylpropionitrile). The solution was stirred for 30 minutes with dry argon and then sealed in a polymerization vessel which was subsequently placed in a constant temperature bath at 70°C. The polymerization vessel was held in the constant temperature bath for three hours throughout which the solution was stirred. The solution was then cooled to room temperature and poured into 4 l. of methanol (a tenfold excess) wherein a white precipitate formed. The precipitate was washed twice with methanol (1 l.) and vacuum dried at 40°C. for 24 hours. 20 g. of a free-flowing white powder was produced which was soluble in acetone, methyl ethyl ketone, benzene, toluene, ethylene glycol monoethyl ether acetate, N,N-dimethylformamide, $\gamma$-butyrolactone, chloroform, 1,1,1-trichloroethane, and numerous other solvents.

EXAMPLE 12

70.0 g. of the PGMC prepared in Example 4 was charged along with toluene (410 ml.) and AIBN (0.21 g.) into a polymerization flask. The flask and the solution were purged with dry argon for 30 minutes and the flask was then sealed and placed in a 70°C. constant temperature bath for 17 hours, during which the solution was constantly stirred. The viscous solution produced was cooled to room temperature and the polymeric product recovered in the manner described in Example 11. 51.5 g. (74% yield) of a white free-flowing powder were recovered.

EXAMPLE 13

60.0 g. of the EGMC prepared in Example 2 was charged into a polymerization flask with toluene (350 ml.) and AIBN (0.25 g.). The solution was purged with dry nitrogen and polymerized at 70°C. in a constant temperature bath while being stirred for a period of 24 hours. The resultant viscous solution was precipitated and the product recovered in the manner described in Example 11, yielding 53.2 g. (88.7% yield) of a white free-flowing powder.

EXAMPLE 14

AIBN (0.25 g.) was added to the solution of EGMC and toluene prepared in Example 6. The solution was then placed in a 500 ml. flask, purged with dry argon for 15 minutes, and polymerized for 20 hours in a 70°C. constant temperature bath. The viscous polymer solution was cooled to room temperature and poured into methanol (1500 ml.). The resulting white precipitate was filtered and washed with two 500 ml. portions of methanol, then vacuum dried at 40°C. for 24 hours.

EXAMPLE 15

385 g. of the monomer prepared in Example 7 was charged into a 4000 ml. flask along with AIBN (1.18 g.) and acetone (2200 ml.). The solution thus produced was purged with dry nitrogen for 15 minutes and polymerized for 24 hours at 70°C. After polymerization, the solution was cooled to room temperature and precipitated in six gallons of isopropyl alcohol. The resulting slurry was stirred for a period of time and then the precipitate was allowed to settle and the supernatant liquid decanted off. The precipitate was washed three times with 2 l. portions of isopropyl alcohol, with the supernatant wash liquor being decanted after each wash. The precipitate was then recovered by filtration and vacuum dried at 40°C. for 24 hours. 315 g. (85% yield) of a white free-flowing powder PGMC polymer was obtained.

EXAMPLE 16

48.2 g. of the EGMC monomer prepared in Example 2, deionized water (116 ml.), and 9.3 g. of a sodium alkyl aryl polyether sulfonate sold as a surfactant under the trade designation "Triton X 200" by the Rohm & Haas Company were charged to a 500 ml. round bottom flask. The mixture was stirred for 10 minutes to form a stable emulsion and ammonium persulfate (0.03 g.) in deionized water (5 ml.) was added to the emulsion. The emulsion was placed under a blanket of nitrogen in a polymerization flask which was held in a constant temperature bath at 90°C. for 1½ hours, during which the emulsion was constantly stirred. The emulsion was then cooled to room temperature and decanted into a 3 l. beaker, leaving 5 g. of gel adhering to the inside surface of the flask. One liter of methanol was added to the emulsion in the beaker, and the resultant mixture stirred for 15 minutes. The emulsion broke, precipitating a white fluffy polymer. This polymer was washed twice with 250 ml. portions of methanol, twice with 250 ml. portions of deionized water, and once again with a 250 ml. portion of methanol. The product was then vacuum dried at 40°C. for 24 hours, yielding 43.2 g. of a white free-flowing powder (about 89% yield).

EXAMPLE 17

48.2 g. of the PGMC monomer prepared in Example 8 was mixed with deionized water (116 ml.), "Triton X 200" (9.2 g.) and ammonium persulfate (0.03 g.) in deionized water (5 ml.). The resultant emulsion was placed in a polymerization flask under a blanket of nitrogen and stirred for 1½ hours at 88°C., the temperature being maintained by placing the polymerization flask in a constant temperature bath. The emulsion was then poured into 1 l. of ethanol and stirred for 15 minutes. This broke the emulsion and 32 g. (67% yield) of a white free-flowing polymeric powder were recovered in the manner described in Example 16.

EXAMPLE 18

48.2 G. of the EGMC monomer prepared in Example 8 was charged to a 500 ml. flask along with deionized water (110 ml.) and 2 g. of a phosphate ester emulsifier sold under the trade designation "Triton QS 44" by the Rohm and Haas Company. The resulting emulsion was stirred for 20 minutes under a blanket of nitrogen at room temperature. One ml. of a 0.15% ferrous sulfate solution in deionized water, 0.25 g. of ammonium persulfate in 5 ml. of deionized water, and 0.1 g. of sodium formaldehyde sulfoxylate in 5 ml. of water were added sequentially to the emulsion. After the addition of these latter reagents, the system warmed by exothermic reaction heat to a temperature of 61°C. in 30 minutes, and was then externally heated to 70°C. in a constant temperature bath and stirred for an hour. The emulsion was cooled and the product polymer recovered therefrom in the manner described in Example 16. 40 g. (83% yield) of a free-flowing white powder was obtained.

EXAMPLE 19

200 G. of PGMC monomer prepared in Example 9 was charged to a 1 l. flask along with 375 ml. of deionized water and 29 g. of a sodium alkyl aryl ether sulfate surfactant sold under the trade designation "Triton X 301" by the Rohm and Haas Company. The mixture was constantly stirred during the addition of these ingredients. The resulting emulsion was purged with nitrogen for 30 minutes and maintained under a blanket of nitrogen throughout the subsequent polymerization period. To the emulsion, at room temperature, were added 2 ml. of 0.15% ferrous sulfate solution, 0.4 g. of ammonium persulfate, and 0.4 g. sodium hydrosulfate (sold under the trade designation "Lykopon" by Rohm and Haas Company), in 5 ml. of water. Through the influence of exothermic heat of reaction, the temperature of the emulsion rose to 65°C. within 20 minutes, and the reaction system was then heated to 70°C. in a constant temperature bath for another 1 hour period. The emulsion was cooled to room temperature and the polymer precipitated therefrom in 2 l. of isopropyl alcohol. The precipitate was washed twice with 500 ml. portions of isopropyl alcohol, twice with 500 ml. portions of deionized water, and once with a 500 ml. portion of isopropyl alcohol, then vacuum dried at 40°C. for 24 hours. 185 g. of a free-flowing white powder (90% yield) was obtained.

EXAMPLE 20

A series of solution copolymerizations of EGMC with various ethylenically unsaturated monomers were conducted in accordance with the procedure described for EGMC homopolymerization in Example 11. The identity and proportions of monomers, solvents and initiators for these copolymerizations are set out in Table 1. Table 1 also shows the polymerization time and temperature and the polymer yield.

Table I

| Comonomer | EGMC | | Comonomer | | Solvent | | AIBN | Temp. | Time | Yield | |
|---|---|---|---|---|---|---|---|---|---|---|---|
| | Grams | Mole | Grams | Mole | Type | ml | Gram | °C | hrs. | Grams | % |
| Acrylic Acid | 19.1 | 0.073 | 1.33 | 0.018 | Acetone | 61 | 0.075 | 70 | 2 | 6.5 | 32 |
| | 17.0 | 0.065 | 3.00 | 0.042 | Acetone | 113 | 0.088 | 60 | 6.1 | 4.0 | 20 |
| | 51.0 | 0.196 | 9.00 | 0.125 | Ethyl Acetate | 350 | 0.263 | 65 | 5 | 2.0 | 33 |
| Maleic Anhydride | 14.8 | 0.057 | 5.57 | 0.057 | Acetone | 61 | 0.057 | 70 | 2.7 | 6.4 | 31 |
| Dimethylamino-ethyl methacrylate | 17.0 | 0.065 | 3.0 | 0.019 | Acetone | 113 | 0.069 | 60 | 12 | 3.2 | 16 |
| | 8.63 | 0.033 | 1.56 | 0.010 | Acetone | 57 | 0.035 | 70 | 6 | 5.5 | 49 |
| Styrene | 4.5 | 0.017 | 0.5 | 0.005 | Benzene | 28 | 0.018 | 70 | 11½ | 2.4 | 53 |
| | 4.0 | 0.015 | 1.0 | 0.010 | Benzene | 28 | 0.021 | 70 | 11½ | 2.4 | 48 |
| | 3.5 | 0.013 | 1.5 | 0.015 | Benzene | 28 | 0.023 | 70 | 11½ | 2.2 | 45 |
| p-Dimethylamino-styrene | 4.25 | 0.016 | 0.7 | 0.005 | Acetone | 28 | 0.017 | 70 | 10 | 2.5 | 49 |
| t-butylamino-ethyl methacrylate | 4.25 | 0.016 | 0.88 | 0.005 | Acetone | 28 | 0.017 | 70 | 6 | 3.2 | 60 |

EXAMPLE 21

A series of copolymers of EGMC with various ethylenically unsaturated monomers were prepared in accordance with the emulsion polymerization procedure described in Example 17, yielding photosensitive copolymers comparable to the homopolymers of EGMC and PGMC. The identities and proportions of monomers and emulsifiers, as well as the conditions and yield of the polymerization reactions are set forth in Table II.

Table II

| Comonomer | EGMC | | Comonomer | | Initiator | Emulsifier | Temp. °C | Time hrs. | Yield | |
|---|---|---|---|---|---|---|---|---|---|---|
| | Grams | Mole | Grams | Mole | | | | | Grams | % |
| Hydroxyethyl-methacrylate | 48.2 | 0.185 | 4.8 | 0.025 | $(NH_4)_2S_2O_8$ | Triton X-200 | 85 | 1.5 | 46.3 | |
| Acrylamide | 48.2 | 0.185 | 12.3 | 0.173 | $(NH_4)_2S_2O_8$ | Triton X-200 | 85 | 1.5 | 49.2 | |

Table II-continued

| Comonomer | EGMC Grams | EGMC Mole | Comonomer Grams | Comonomer Mole | Initiator | Emulsifier | Temp. °C | Time hrs. | Yield Grams % |
|---|---|---|---|---|---|---|---|---|---|
| n-Butyl Acrylate | 48.2 | 0.185 | 23.7 | 0.204 | $(NH_4)_2S_2O_8$ | Triton X-200 | 85 | 1.5 | 78.2 |
|  | 48.2 | 0.185 | 14.2 | 0.122 | $(NH_4)_2S_2O_8$ | Triton X-200 | 85 | 1.5 | 58.6 |
| Acrylamide | 48.2 | 0.185 | 3.27 | 0.046 | $(NH_4)_2S_2O_8$ | Triton X-200 | 85 | 1.5 | 47.9 |
| Methacrylic Acid | 48.2 | 0.185 | 4.82 | 0.056 | $(NH_4)_2S_2O_8$ | Triton X-200 | 85 | 1.5 | 51.0 |

EXAMPLE 22

EGMC monomer (4 g.), styrene (0.5 g.) and acrylic acid (0.5 g.) were charged into a vessel containing acetone (28 ml.) and AIBN (0.0222 g.). The solution was held at 70°C. for 9½ hours. 2.2 g. of the resulting terpolymer (45% yield) was recovered in accordance with the method described in Example 11.

EXAMPLE 23

To a 15% solution in benzene of the product formed in Example 10, 0.05 mole percent AIBN was added. The vessel was purged with nitrogen, sealed and maintained at 70°C. for 10 hours. The resulting polymer was recovered in the manner described in Example 11. A 40% yield was obtained.

EXAMPLE 24

A 50/50 solution in benzene of the EGMC monomer formed in Example 3 and the phenyl substituted EGMC formed in Example 10 was prepared containing 15½% by weight total monomers and 0.05 mole percent AIBN. The vessel was purged with nitrogen, sealed and maintained at 70°C. for 4 hours. The resulting polymer was recovered in the manner described in Example 11. A 30% yield was obtained.

EXAMPLE 25

A coating solution was prepared containing 2% by weight of the polymer prepared in Example 11 and 0.2% of 4,4'-dimethylaminobenzophenone in chloroform. This solution was applied by means of a whirler to a brush grained aluminum plate which had been anodized for 4 minutes in 25% sulfuric acid at 100°F. and 18 amps/sq.ft. a.c. The chloroform was allowed to evaporate and, after the plate was thoroughly dried, it was exposed to a carbon arc through a half-tone negative for a period sufficient to absorb 20 lux units of actinic light. The exposed plate was developed with a 50/50 solution of gum arabic and ethylene glycol monoethyl ether acetate, then dried and placed on an offset press. The plate provided 80,000 good impressions and showed little, if any, wear on the image areas.

EXAMPLE 26

A coating solution was prepared containing 2% by weight of the EGMC produced in Example 16 and 0.2% by weight of 4,4'-dimethylaminobenzophenone in methyl ethyl ketone. This coating solution was applied by means of a whirler to a brush grained plate which had been previously dipped in a 5% by weight sodium silicate solution for 30 seconds at 170°F. After the plate was dried and exposed, noncrosslinked polymer was removed from the plate with a solution containing 70% 14°Be gum arabic, 20% γ-butyrolactone, and 10% benzyl alcohol. The plate was mounted on an offset press and produced satisfactory copies in printing tests.

EXAMPLE 27

An electrochemically grained aluminum base plate was anodized in a 15% sulfuric acid solution for 3 minutes at a temperature of 90°F. and an a.c. current density of 23 amps./sq. ft. A coating solution containing 3% by weight of the photopolymer formed in Example 13, 0.3% diethylaminobenzophenone, and 0.15% naphthol red B pigment in toluene was applied to the grained anodized base plate and the coating was dried. After drying, the plate was exposed through a half-tone negative and developed with a 70/30 14°Be gum arabic/cyclohexanone mixture. The plate was mounted on an offset press and 150,000 excellent copies were run with no deterioration of the image areas.

EXAMPLE 28

A paper plate manufactured by the S. D. Warren Company and sold under the trade designation "Fotoramic 12" was washed thoroughly to remove all traces of the sensitizer coated on the surface, and was whirl coated with a coating solution containing 2% by weight of the polymer produced in Example 14 and 0.3% dimethylaminobenzophenone in benzene. After drying and exposure, the plate was swabbed with a developing solution containing 75% by weight 14°Be gum arabic, 15% by weight butyrolactone, and 10% by weight ethylene glycol monoethyl ether acetate. This plate provided 25,000 good impressions before the nonimage areas began to become sensitive and take ink.

EXAMPLE 29

A coating solution was prepared containing 4% of the polymer formed in Example 15 and 0.2% 4,4'-dimethylaminobenzophenone in benzene. This coating solution was applied by means of a roller coater to a brush grained aluminum base plate which had been anodized in 25% phosphoric acid at 70° F. for six minutes at a direct current density of 14 amps./sq. ft. After drying and exposure, the plate was developed with an emulsion containing 35% water, 35% 1,1,1-trichloroethane and 30% ethylene glycol monomethyl ether. This plate was used in a run of 100,000 excellent copies with no deterioration of the image areas.

EXAMPLE 30

EGMC monomer (41.1 g.) and AIBN (0.2 g.) were charged to a screw-capped bottle which was flushed with nitrogen, sealed, and placed in a controlled temperature bath at 36°–39°C. After 19 hours, the polymer was withdrawn from the bath and mixed with methyl ethyl ketone, in which it proved to be sparingly soluble. Dimethylformamide was mixed with the remaining solid polymer and another small proportion of that polymer was dissolved in the latter solvent. Soluble polymer recovered from these two solutions, containing 10% by weight DEAB, was exposed to actinic light and found to be photosensitive.

EXAMPLE 31

EGMC monomer (41 g.), normal butyl acrylate (4.8 g.) and AIBN (0.2 g.) were charged to a reaction bottle. The bottle was flushed with nitrogen, sealed and placed in a constant temperature bath at 32°C. for 23 hours. The polymer produced was found to be sparingly soluble in both acetone and dimethylformamide. The soluble polymer was recovered from these two solvents and a mixture of this polymer containing 10% by weight DEAB was exposed to actinic light. It proved to be photosensitive.

EXAMPLE 32

EGMC (41 g.), methacrylic acid (4.8 g.) and AIBN (12.2 g.) were added to a flask and polymerized in bulk under a blanket of nitrogen for 25 hours at 32°C. The polymer formed was sparingly soluble in dimethylformamide and acetone. The polymer recovered from these solvents was sensitized with 10% by weight DEAB and exposed to actinic light. It proved to be photosensitive.

EXAMPLE 33

A screw-capped bottle was charged with EGMC monomer (41 g.), normal butyl acrylate (2.4 g.), methacrylic acid (2.4 g.), and AIBN (0.2 g.). After 24 hours at 32°C., the resultant polymer was added to dimethylformamide and found to be slightly soluble. The soluble polymer was recovered from the solvent. A mixture of this polymer containing 10% by weight DEAB was exposed to light and proved to be photosensitive.

EXAMPLE 34

A 500 ml. three necked flask equipped with a stirring rod and condenser with drying tube was charged with water (161 g.), sodium lauryl sulfate (0.03 g.), sodium sulfate (1.3 g.), EGMC monomer (48.2 g.), stearic acid (0.5 g.), and benzoyl peroxide (0.26 g.). The mixture was stirred under nitrogen for 1.5 hours at 80°C. A substantial quantity of poly EGMC (52.4 g. wet) precipitated during the reaction. This polymer was collected, washed with water and dried. The polymer was mixed with dimethylformamide and a small proportion proved to be soluble. The dissolved polymer was recovered from the dimethylformamide, mixed with 10% by weight DEAB, exposed to light, and found to be photosensitive.

EXAMPLE 35

Methacrylic acid (86 g.), 1,2-epoxybutane (36 g.), and a 40% solution of benzyltrimethylammoniummethoxide in methanol (21 g.) were charged to a round bottom flask and stirred at room temperature for 98 hours. 300 ml. of a 7% sodium hydroxide solution and 200 ml. of ethyl acetate were added to the mixture, the organic layer separated, and the basic aqueous layer given a second wash with 200 ml. of ethyl acetate. The organic fractions were then combined, and washed successively with 300 ml. of 7% sodium hydroxide and three 200 ml. portions of water, the spent wash solutions being decanted between washings. Excess moisture was removed from the washed organic phase with sodium sulfate and the ethyl acetate was stripped off to yield hydroxybutyl methacrylate (41 g.). This product was taken up in 60 ml. of benzene and pyridine (22 g.). Cinnamoyl chloride (50.4 g.) in 75 ml. of benzene was added dropwise with stirring to the hydroxybutyl methacrylate solution and the resulting mixture allowed to react for a period of 24 hours. After the reaction was complete pyridine hydrochloride formed by the reaction was filtered off, the filtrate washed and the product cinnamoylated hydroxybutyl methacrylate recovered in the manner described in Example 8.

An emulsion was prepared containing this cinnamoylated hydroxybutyl methacrylate (28 g.), "Triton X-200" (6 g.), ammonium persulfate (0.03 g.), in 18 ml. of methanol and 75 ml. of water. The emulsion was purged with nitrogen and held at temperature of 82°–92°C. for 3½ hours causing a polymer to form. The polymer was precipitated from the emulsion by the addition of 2 liters of methanol. After precipitation, the polymer was washed and dried to yield 19.5 g. of cinnamoylated hydroxybutyl methacrylate homopolymer. When applied to the surface of an anodized aluminum base plate this polymer provided a satisfactory lithographic plate.

EXAMPLE 36

Methacrylic acid (43 g.), 1,2-epoxy, 3-phenoxy propane (37.5 g.), and benzyltriethylammonium chloride (5.2 g.) in 10 g. of methanol were charged to a round bottom flask. The flask was flushed with nitrogen, sealed, and stirred at room temperature for 140.5 hours. 1-hydroxy, 3-phenoxypropyl methacrylate (55.7 g.) was recovered from the resulting reaction mixture in accordance with the method described in Example 35, cinnamoylated with cinnamoyl chloride, and the resulting monomer (60 g.) recovered in the manner described in Example 1. 15 G. of this thick yellow monomer was taken up in 100 ml. of benzene and AIBN (0.15 g.) was added to the mixture in a polymerization flask. The flask was flushed with nitrogen and stirred at 72°C. for 24 hours. After the polymerization reaction was complete, the solution was added dropwise into a stirred methanol solution thereby causing the polymer to precipitate. The precipitated polymer was collected by filtration, washed with methanol and dried, yielding 6.4 g. of cinnamoylated phenoxypropyl methacrylate. Several lithographic plates were prepared using this polymer, all of which gave acceptable performance.

EXAMPLE 37

Cinnamoyl chloride (52.5 g.) in 100 ml. of benzene was added dropwise with stirring over a period of one hour to a solution containing hydroxyethyl acrylate (30 g.) and pyridine (25 g.) in another 100 ml. of benzene. The resulting mixture was stirred for another two hours to complete the reaction. The pyridine hydrochloride formed by the reaction was filtered from the solution and the filtrate washed successively with three 250 ml. portions of 5% sodium hydroxide solution, three 250 ml. portions of 5% hydrochloric acid solution, and three 250 ml. portions of deionized water. The washed filtrate containing the cinnamoylated monomer was then dried over anhydrous calcium chloride to yield 294 ml. of solution.

A 100 ml. portion of the solution containing the monomer was diluted with 200 ml. of benzene, AIBN (0.2 g.) was added, and the solution was polymerized under a blanket of nitrogen for 8 hours at 73°C. The polymer was precipitated from the reaction solution by addition of a ten-fold excess of methanol, recovered by filtration and dried to yield a free-flowing white powder.

1 G. of the dried polymer was dissolved in 30 ml. of methyl ethyl ketone and Michler's ketone (0.1 g.) was added. The resulting solution was whirl coated at 78 rpm on an electrochemically grained anodized plate, dried, and exposed through a negative. The exposed plate was developed with a 25% γ-butyrolactone solution in 14° Be gum arabic and gave an acceptable image.

EXAMPLE 38

A solution containing glacial methacrylic acid (86 g.), epichlorohydrin (46.25 g.), and a 40% solution of benzyltrimethylammonium chloride in methanol (21 g.) was stirred in a 250 ml. Erlenmeyer flask for 6 days. The solution was then transferred to a 1 liter beaker and stirred for 30 minutes with a 12.5% sodium hydroxide solution (250 ml.) and ethyl acetate (200 ml.). The organic layer was removed and the aqueous layer was washed with two 100 ml. portions of ethyl acetate. All the organic fractions were then combined and washed successively with 2 × 200 ml. portions of 7% aqueous sodium hydroxide and 4 × 200 ml. portions of deionized water. The washed solution was dried over anhydrous sodium sulfate and the ethyl acetate was stripped off on a rotary evaporator to yield 83 g. of a colorless slightly viscous product whose i.r. spectrum was consistent with 3-chloro, 2-hydroxypropyl methacrylate.

EXAMPLE 39

60 G. of the hydroxy ester produced in Example 38, pyridine (27.5 g.), and benzene (100 ml.) were charged to a 250 ml. round bottom flask. Cinnamoyl chloride (60 g.) in benzene (100 ml.) was then added to the hydroxy ester solution, with stirring, over a one hour period. The resulting slurry was stirred for an additional two hours and a slightly yellow viscous product (81 g.) recovered therefrom in accordance with the method described in Example 8. The i.r. spectrum of this product showed no hydroxyl bond and was consistent with chloropropylene glycol methacrylate cinnamate.

60 G. of the chloropropylene glycol methacrylate cinnamate, benzene (450 ml.) and AIBN (0.25 g.) were added to a polymerization vessel. The resulting solution was purged with nitrogen and then held at 70°C. for 24 hours to effect polymerization. The polymerized product was recovered by dropwise addition of the polymerization reaction mixture to 5 liters of well-agitated methanol. The white precipitate which formed was washed with 2 × 1500 ml. portions of methanol and vacuum dried at 40°C. for 24 hours to yield 52 g. of a free-flowing white powder.

EXAMPLE 40

A solution containing 3% by weight of the polymer produced in Example 39 and 0.3% by weight Michler's ketone in ethylene glycol monoethyl ether acetate was whirl coated at 78 rpm onto an aluminum plate which had been brush grained and A.C. anodized in a sulfuric acid solution. The coated plate was exposed through a half-tone negative to 40 lux of u.v. radiation emitted by a carbon arc. The plate was developed with a solution containing 80% γ-butyrolactone and 20% water. The developed plate was gummed and then subjected to a press test in which it gave 100,00 excellent impressions with no visible signs of wear.

EXAMPLE 41

1-Naphthyl acrylic acid was prepared by reaction of 1-naphthaldehyde and malonic acid. 1-Naphthaldehyde (46.8 g.), malonic acid (60.0 g.), pyridine (120 ml.), and piperidine (3 ml.) were charged into a 500 ml. round bottom flask and refluxed on a water bath for 4 hours. The reaction solution was cooled to room temperature and poured onto a mixture of 175 ml. concentrated hydrochloric acid and 300 g. of crushed ice. A white precipitate formed and the slurry was stirred until all the ice had melted. The precipitate was separated from the slurry by filtration and washed with one portion of 10% hydrochloric acid (75 ml.) and two portions of deionized water (each 75 ml.). The 1-naphthyl acrylic acid precipitate was fully dewatered by continued application of suction on the filter, and then vacuum dried at 40°C. for 24 hours.

1-Naphthyl acrylic acid (33.1 g.), thionyl chloride (33 ml.), and benzene (300 ml.) were charged into a 500 ml. flask and refluxed for 2 hours. The benzene and excess thionyl chloride were then distilled leaving a yellow residue of 1-naphthyl acryloyl chloride.

EXAMPLE 42

A solution of 1-naphthyl acryloyl chloride (15.0 g.) in benzene (15 ml.) was added dropwise over a one hour period to a solution of hydroxyethyl methacrylate (12.4 g.), pyridine (7.5 ml.), and benzene (7.5 ml.). The resulting slurry was stirred for a further one and one-half hours. Pyridine hydrochloride was filtered off and the monomer, ethylene glycol methacrylate 1-naphthyl acrylate, was recovered in the manner described in Example 8.

13.9 G. of this monomer was added to deionized water (35 ml.), Triton X-200 (3.7 g.), methanol (8 ml.), and ammonium persulfate (0.01 g.). The resulting emulsion was stirred at 88°C. for 2 hours under a nitrogen blanket. A polymer was produced which was precipitated from the emulsion by the addition of excess methanol, separated from the emulsion slurry by filtration and dried. 5.0 G. of polymer were obtained. A solution containing 3% of this polymer and 0.3% of DEAB in dimethylformamide was applied to a brush grained aluminum plate which had been A.C. anodized in sulfuric acid. The lithographic plate thus produced was exposed for 2 minutes through a half tone negative to u.v. light emitted by a carbon arc. The plate was then developed with a 50% ethylene glycol monoethyl ether acetate in gum arabic to produce a hard, ink-receptive image.

EXAMPLE 43

2-Furyl acrylic acid was prepared by reaction of furfural and malonic acid. Furfural (19.2 g.), malonic acid (41.6 g.), pyridine (100 ml.), and piperidine (2 ml.) were charged into a 250 ml. round bottom flask and refluxed for 3½ hours. The reaction solution was worked up in the manner described in Example 41 to isolate 2-furyl acrylic acid.

EXAMPLE 44

2-Furyl acrylic acid (13.8 g.), hydroxyethyl methacrylate (13 g.), p-toluene sulfonic acid (6.5 g.), pyrogallol (0.65 g.), copper powder (0.01 g.), and benzene (200 ml.) were charged to a 500 ml. round bottom flask. A Dean-Stark trap and condenser were attached to the flask and the mixture contained in the flask was cyclicly distilled for 6 hours (until no more water distilled over). The reaction mixture was cooled to room temperature and filtered to remove a small amount of polymer which formed. The clarified solution was washed twice with 500 ml. portions of saturated sodium carbonate solution, twice with 500 ml. portions of deionized water, and then processed in the manner described in Example 8 to recover the product. 17.5 G. of product were recovered. IR analysis showed no hydroxyl bond and strong ester and furan peaks, consistent with ethylene glycol methacrylate 2-furyl acrylate.

15.0 G. of ethylene glycol methacrylate 2-furyl acrylate was dissolved in benzene (100 ml.) and AIBN (0.05 g.) was added. The solution was polymerized at 70°C. under nitrogen for 5 hours. A polymer which formed was precipitated in 500 ml. of methanol and washed twice with 200 ml. portions of methanol, then vacuum dried at 40°C. over night. 5 g. of polymer were obtained.

A portion of this polymer (3 g.) and DEAB (0.3 g.) were dissolved in methyl ethyl ketone (100 ml.) and coated onto a brush grained aluminum plate which had been D.C. anodized in phosphoric acid. The coated plate was exposed through a negative master to 40 lux of u.v. radiation. The plate was developed with a solution of 30% γ-butyrolactone in 14° gum arabic to give a hard, ink-receptive image.

EXAMPLE 45

2-thienyl acrylic acid was prepared by reaction of 2-thiophene carboxaldehyde with malonic acid. A solution of 2-thiophene carboxaldehyde (25.7 g.), malonic acid (41.6 g.), pyridine (100 ml.), and piperidine (2 ml.) was refluxed for 3½ hours. 2-thienyl acrylic acid was recovered from the reaction mixture in a manner parallel to that described in Example 41.

EXAMPLE 46

2-thienyl acrylic acid (15.4 g.), hydroxybutylene glycol methacrylate (15.8 g.), p-toluene sulfonic acid (6.25 g.), pyrogallol (0.65 g.), copper powder (0.1 g.), and benzene (200 ml.) were cyclicly distilled in a 500 ml. flask over a period of 9 hours. The reaction mixture was then cooled to room temperature and ethylene glycol methacrylate 2-thienyl acrylate recovered from the reaction mixture in a manner parallel to that described in Example 44. 21.5 G. of monomer were recovered.

A solution containing ethylene glycol methacrylate 2-thienyl acrylate (15.0 g.) and AIBN (0.05 g.) in benzene (100 ml.) was held at 70°C for 9 hours to polymerize the monomer. The reaction solution was then poured into 1 l. of methanol to precipitate the off-white polymer. The polymer was filtered and dried. 10.5 G. were obtained.

An electrochemically grained aluminum plate which had been D.C. anodized in phosphoric acid was coated with a 2.5% solution of polyethylene glycol methacrylate 2-thienyl acrylate containing 0.25% by weight DEAB. After exposure and development this plate gave a good image.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

What is claimed is:

1. A compound represented by the general formula:

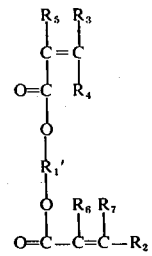

wherein $R_1'$ is selected from the group consisting of alkylene, haloalkylene, alkoxyalkylene, aminoalkylene, cycloalkylene, aralkylene, cycloalkylakylene and aryloxyalkylene groups, $R_2$ is selected from the group consisting of substituted or unsubstituted aryl groups wherein the substituents are selected from the group consisting of alkyl, methoxy, chloro, bromo and nitro, $R_3$, $R_4$ and $R_5$ are each selected from the group consisting of hydrogen, halogen and lower alkyl, and $R_6$ and $R_7$ are each selected from the group consisting of hydrogen, halogen, nitro, lower alkyl, phenyl, phenoxy, and lower alkoxy.

2. A compound as set forth in claim 1 wherein $R_1'$ is alkylene or aralkylene, $R_2$ is phenyl, methoxyphenyl or m-nitrophenyl, $R_3$ is hydrogen, $R_4$ is hydrogen or methyl, $R_5$ is hydrogen or lower alkyl, and $R_6$ and $R_7$ are each hydrogen or lower alkyl.

3. The compound as set forth in claim 2 wherein $R_1'$ is ethylene, $R_2$ is phenyl, $R_3$ is hydrogen, $R_4$ is hydrogen, $R_5$ is methyl, and $R_6$ and $R_7$ are hydrogen.

4. The compound as set forth in claim 2 wherein $R_1'$ is propylene, $R_2$ is phenyl, $R_3$ is hydrogen, $R_4$ is hydrogen, $R_5$ is methyl, and $R_6$ and $R_7$ are hydrogen.

5. The compound as set forth in claim 2 wherein $R_1'$ is phenylethylene, $R_2$ is phenyl, $R_3$ is hydrogen, $R_4$ is hydrogen, $R_5$ is methyl, and $R_6$ and $R_7$ are hydrogen.

6. A compound as set forth in claim 2 wherein $R_1'$ is ethylene, $R_2$ is phenyl, and $R_3$, $R_4$, $R_5$, $R_6$ and $R_7$ are each hydrogen.

7. A compound as set forth in claim 2 wherein $R_1'$ is propylene, $R_2$ is phenyl, and $R_3$, $R_4$, $R_5$, $R_6$ and $R_7$ are each hydrogen.

8. A compound as set forth in claim 2 wherein $R_1'$ is ethylene, $R_2$ is m-nitrophenyl, $R_3$ is hydrogen, $R_4$ is hydrogen, $R_5$ is methyl, and $R_6$ and $R_7$ are each hydrogen.

9. α-Phenylhydroxyethyl methacrylate.

10. β-Phenylhydroxyethyl methacrylate.

11. A compound represented by the general formula:

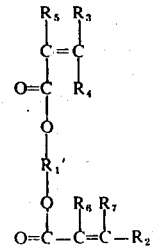

wherein $R_1'$ is selected from the group consisting of alkylene, haloalkylene, alkoxyalkylene, aminoalkylene, cycloalkylene, aralkylene, cycloalkylalkylene and aryloxyalkylene groups, $R_2$ is unsubstituted aryl, $R_3$, $R_4$ and $R_5$ are each selected from the group consisting of hydrogen, halogen and lower alkyl, and $R_6$ and $R_7$ are each selected from the group consisting of hydrogen, halogen, nitro, lower alkyl, phenyl, phenoxy, and lower alkoxy.

* * * * *